US008502001B2

(12) United States Patent
Daniel et al.

(10) Patent No.: US 8,502,001 B2
(45) Date of Patent: Aug. 6, 2013

(54) PROCESS FOR THE PRODUCTION OF ALCOHOL FROM A CARBONACEOUS FEEDSTOCK

(75) Inventors: Berian John Daniel, Beverley (GB); Benjamin Patrick Gracey, Hull (GB)

(73) Assignee: BP P.L.C., London (GB)

( * ) Notice: Subject to any disclaimer, the term of this patent is extended or adjusted under 35 U.S.C. 154(b) by 171 days.

(21) Appl. No.: 12/734,610

(22) PCT Filed: Nov. 7, 2008

(86) PCT No.: PCT/GB2008/003771
§ 371 (c)(1),
(2), (4) Date: May 12, 2010

(87) PCT Pub. No.: WO2009/063176
PCT Pub. Date: May 22, 2009

(65) Prior Publication Data
US 2011/0046421 A1 Feb. 24, 2011

(30) Foreign Application Priority Data
Nov. 14, 2007 (EP) .................................. 07254447

(51) Int. Cl.
*C07C 29/149* (2006.01)

(52) U.S. Cl.
USPC .......................................... 568/885; 568/884

(58) Field of Classification Search
USPC ................................................... 568/884, 885
See application file for complete search history.

(56) References Cited

FOREIGN PATENT DOCUMENTS

| DE | 32 21 077 | 12/1983 |
|----|-----------|---------|
| EP | 0 082 692 | 6/1983 |
| EP | 0 167 300 | 1/1986 |
| GB | 385 625 | 1/1933 |
| WO | 83/03409 | 10/1983 |

OTHER PUBLICATIONS

International Search Report for PCT/GB2008/003771, mailed Apr. 8, 2009.
Written Opinion of the International Searching Authority for PCT/GB2008/003771, mailed Apr. 8, 2009.
International Preliminary Report on Patentability for PCT/GB2008/003771, mailed Feb. 24, 2010.

*Primary Examiner* — Brian J Davis
(74) *Attorney, Agent, or Firm* — Nixon & Vanderhye

(57) ABSTRACT

Process for the conversion of ethanoic acid into ethanol by (a) introducing ethanoic acid and $H_2$ into a primary hydrogenation unit in the presence of a precious metal-based catalyst to produce ethanol and ethyl ethanoate and (b) introducing ethyl ethanoate, from step (a), together with $H_2$ into a secondary hydrogenation unit in the presence of a copper-based catalyst to produce ethanol. Ethanol from step (b) is recovered.

34 Claims, 2 Drawing Sheets

PROCESS FOR THE PRODUCTION OF ALCOHOL FROM A CARBONACEOUS FEEDSTOCK

This application is the U.S. national phase of International Application No. PCT/GB2008/003771, filed 7 Nov. 2008, which designated the U.S. and claims priority to European Application No. 07254447.1, filed 14 Nov. 2007, the entire contents of each of which are hereby incorporated by reference.

The present invention relates to a process for the production of ethanol from ethanoic acid.

In particular the present invention relates to a process for the production of ethanol from a carbonaceous feedstock, wherein the carbonaceous feedstock is first converted to synthesis gas which is then converted to ethanoic acid, which is then subject to a two stage hydrogenation process by which at least a part of the ethanoic acid is converted by a primary hydrogenation process into ethyl ethanoate which ethyl ethanoate is converted by a secondary hydrogenation process to produce ethanol.

BACKGROUND OF THE INVENTION

In recent years increased use and demand for alcohols such as methanol, ethanol and higher alcohols has led to a greater interest in processes relating to alcohol production. The said alcohols may be produced by the fermentation of, for example, sugars and/or cellulosic materials.

Alternatively alcohols, such as ethanol, may be produced from synthesis gas. Synthesis gas refers to a combination of $H_2$ and carbon oxides produced in a synthesis gas plant from a carbon source such as natural gas, petroleum liquids, biomass and other carbonaceous materials including coal, recycled plastics, municipal wastes, or any organic material. Thus, alcohol and alcohol derivatives may provide non-petroleum based routes for the production of valuable chemicals and fuels.

Generally, the production of alcohols, for example methanol, takes place via three process steps: synthesis gas preparation, methanol synthesis, and methanol purification. In the synthesis gas preparation step, an additional stage may be employed whereby the feedstock is treated, e.g. the feedstock is purified to remove sulphur and other potential catalyst poisons prior to being converted into synthesis gas. This treatment can also be conducted after synthesis gas preparation; for example, when coal or biomass is employed.

The reaction to produce alcohol(s) from synthesis gas is generally exothermic. The formation of $C_2$ and $C_{2+}$ alcohols is believed to proceed via the formation of methanol for modified methanol catalysts and cobalt molybdenum sulphide catalysts. However, the production of methanol is equilibrium-limited and thus requires high pressures in order to achieve viable yields. Hence, pressure can be used to increase the yield, as the reaction which produces methanol exhibits a decrease in volume, as disclosed in U.S. Pat. No. 3,326,956.

A low-pressure, copper-based methanol synthesis catalyst is commercially available from suppliers such as BASF, Johnson Matthey, and Haldor-Topsoe. Methanol yields from copper-based catalysts are generally over 99.5% of the converted $CO+CO_2$ present. Water is a by-product of the conversion of $CO_2$ to methanol and the conversion of CO synthesis gas to $C_2$ and $C_{2+}$ oxygenates. In the presence of an active water-gas shift catalyst, such as a methanol catalyst or a cobalt molybdenum catalyst the water equilibrates with the CO to give $CO_2$ and $H_2$. A paper entitled, "Selection of Technology for Large Methanol Plants," by Helge Holm-Larsen, presented at the 1994 World Methanol Conference, Nov. 30-Dec. 1, 1994, in Geneva, Switzerland, reviews the developments in methanol production and shows how further reduction in costs of methanol production will result in the construction of very large plants with capacities approaching 10,000 t per day.

Other processes for the production of $C_2$ and $C_{2+}$ alcohol(s), include the processes described hereinafter; U.S. Pat. No. 4,122,110 relates to a process for manufacturing alcohols, particularly linear saturated primary alcohols, by reacting CO with $H_2$ at a pressure between 2 and 25 MPa and a temperature between 150 and 400° C., in the presence of a catalyst, characterized in that the catalyst contains at least 4 essential elements: (a) copper (b) cobalt (c) at least one element M selected from chromium, iron, vanadium and manganese, and (d) at least one alkali metal.

U.S. Pat. No. 4,831,060 relates to the production of mixed alcohols from CO and $H_2$ gases using a catalyst, with optionally a co-catalyst, wherein the catalyst metals are molybdenum, tungsten or rhenium, and the co-catalyst metals are cobalt, nickel or iron. The catalyst is promoted with a Fischer-Tropsch promoter like an alkali or alkaline earth series metal or a smaller amount of thorium and is further treated by sulfiding. The composition of the mixed alcohols fraction can be selected by selecting the extent of intimate contact among the catalytic components.

Journal of Catalysis 1988, 114, 90-99 discloses a mechanism of ethanol formation from synthesis gas over $CuO/ZnO/Al_2O_3$. The formation of ethanol from CO and $H_2$ over a CuO/ZnO methanol catalyst is studied in a fixed-bed microreactor by measuring the isotopic distribution of the carbon in the product ethanol when isotopically-enriched $^{13}$C methanol was added to the feed.

SUMMARY OF THE INVENTION

As the importance of ethanol is ever increasing in today's world, so is the need and desire to produce ethanol with a higher carbon efficiency, a higher conversion and an improved selectivity from a carbonaceous feedstock. Hence, the present invention provides a process that allows one to produce ethanol from a carbonaceous feedstock, with improved carbon efficiency, a higher selectivity and, in particular, with a more efficient conversion to ethanol, including a more efficient process step for the conversion of ethanoic acid to ethanol.

BRIEF DESCRIPTION OF THE DRAWINGS

The invention is further described with reference to the accompanying drawings, in which.

Figure 1:
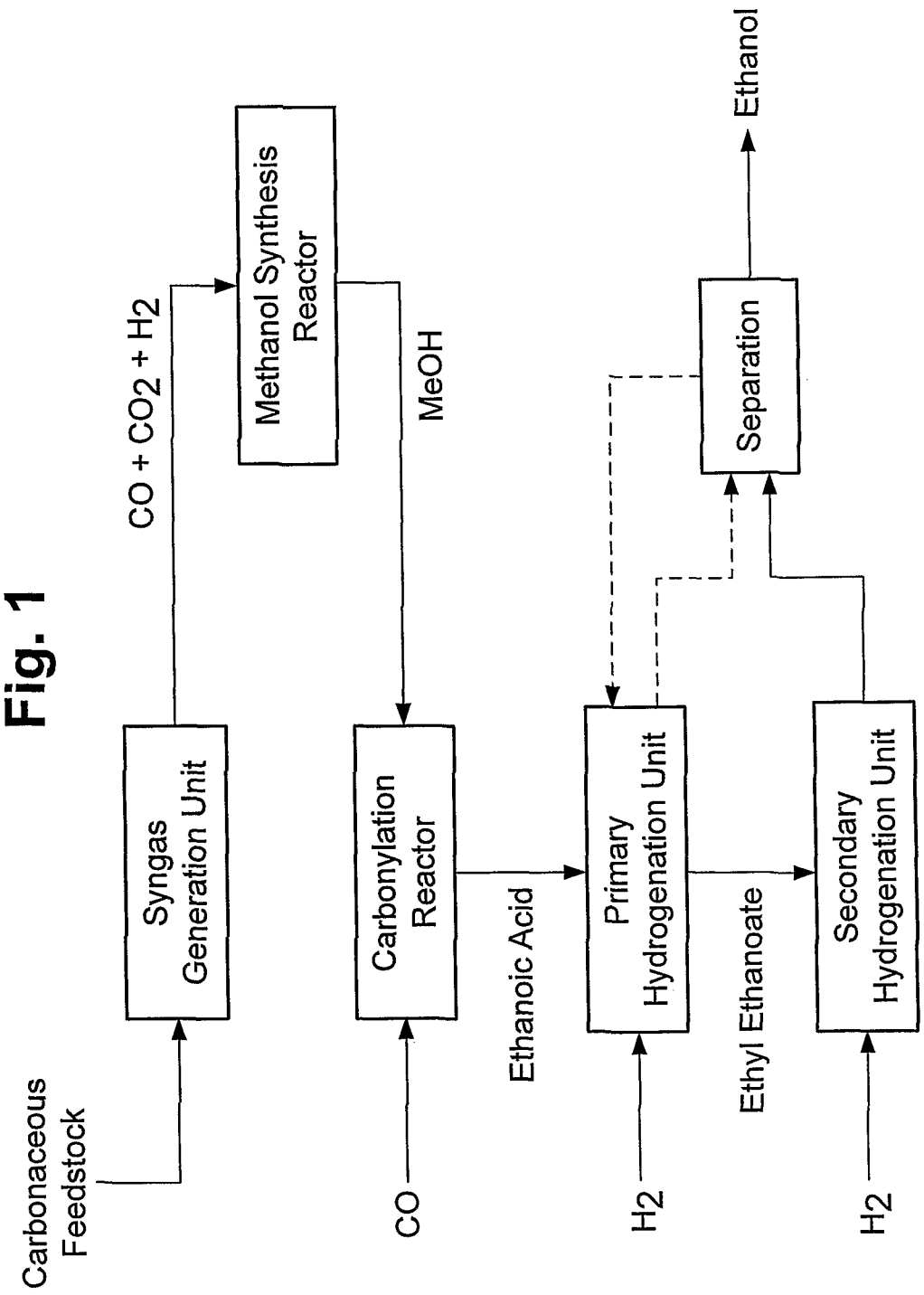
FIGS. 1 and 2 represent embodiments of a process scheme according to the present invention wherein the references correspond to those used in the present description and appending claims.

Thus, the present invention provides a process for the conversion of ethanoic acid into ethanol characterised by the following steps:
1. introducing ethanoic acid and $H_2$ into a primary hydrogenation stage in the presence of a precious metal-based catalyst to produce ethanol and ethyl ethanoate,
2. introducing ethyl ethanoate, from step 1, together with $H_2$, into a secondary hydrogenation stage in the presence of a copper-based catalyst to produce ethanol, and
3. recovering ethanol from step 2.

The present invention also provides a process for the conversion of methanol into ethanol, characterised by the following steps:
1. introducing methanol, together with CO, into a carbonylation reactor to produce ethanoic acid,
2. introducing ethanoic acid, from step 1, together with $H_2$, into a primary hydrogenation unit in the presence of a precious metal-based catalyst to produce ethanol and ethyl ethanoate,
3. introducing ethyl ethanoate from step 2, together with H2, into a secondary hydrogenation unit in the presence of a copper-based catalyst to produce ethanol, and
4. recovering ethanol from step 3.

Furthermore, the present invention provides a process for the conversion of a carbonaceous feedstock into ethanol, whereby the carbonaceous feedstock is first converted into synthesis gas, which is subsequently converted into ethanol, characterised by the following consecutive steps:
1. introducing a carbonaceous feedstock, into a synthesis gas generation unit to produce synthesis gas,
2. introducing synthesis gas, produced in step 1, into a methanol synthesis reactor, to produce methanol,
3. introducing methanol, from step 2, together with CO, into a carbonylation reactor, to produce ethanoic acid,
4. introducing ethanoic acid, from step 3, together with $H_2$, into a primary hydrogenation unit in the presence of a precious metal-based catalyst, to produce ethanol and ethyl ethanoate,
5 introducing ethyl ethanoate, from step 4, together with $H_2$, into a secondary hydrogenation unit in the presence of a copper-based catalyst, to produce ethanol, and
6. recovering ethanol from step 5.

For the purposes of the present invention and appending claims the following terms are defined hereinafter:

The 'dew point temperature' is a threshold temperature, for example, for a given pure component or mixture of components, at a given pressure, if the system temperature is raised to above the dew point temperature, the mixture will exist as a dry gas. Likewise below the dew point temperature, the mixture will exist as a vapour containing some liquid.

'Gas' and/or 'gas phase' are defined as a pure component, or mixture of components, that are above the dew point temperature.

'Gas hourly space velocity' (GHSV) is defined as the volume of gas fed, per unit volume of catalyst per hour, at standard temperature (0° C.) and pressure (0.101325 MPa). 'Liquid hourly space velocity' (LHSV) is defined as the volume of liquid fed, per unit volume of catalyst per hour.

According to one aspect of the present invention, the synthesis gas feedstock, a mixture of carbon oxide(s) and $H_2$, that is used to produce the methanol feed stream, is preferably produced from a carbonaceous feedstock.

The carbonaceous feedstock is preferably a material such as biomass, plastic, naphtha, refinery bottoms, crude synthesis gas (from underground coal gasification or biomass gasification), smelter off gas, municipal waste, coal bed methane, coal, and/or natural gas, with coal and natural gas being the preferred sources. To one skilled in art a combination of sources can also be used, for example coal and natural gas to advantageously increase the $H_2$ to carbon ratio.

Natural gas commonly contains a range of hydrocarbons (e.g. $C_1$-$C_3$ alkanes), in which methane predominates. In addition to this, natural gas will usually contain nitrogen, $CO_2$ and sulphur compounds. Preferably the nitrogen content of the feedstock is less than 40 mol %, more preferably less than 10 mol % and most preferably less than 2 mol %.

Processes for producing synthesis gas, in a synthesis gas plant, are well known. Each method has its advantages and disadvantages, and the choice of using a particular reforming process over another is governed by economic and available feed stream considerations, as well as by the desire to obtain the optimum ($H_2$—$CO_2$):($CO$+$CO_2$) molar ratio in the resulting synthesis gas that is suitable for further chemical processing. A discussion of the available synthesis gas production technologies is provided in both Hydrocarbon Processing, 1999, 78:4, 87-90, and 92-93 and Petrole et Techniques, 1998, 415, 86-93, and are both hereby incorporated by reference.

It is also known that the synthesis gas may be obtained by catalytic partial oxidation of hydrocarbonaceous material in a microstructured reactor as exemplified in IMRET 3: Proceedings of the Third International Conference on Microreaction Technology, ed. W. Ehrfeld, Springer Verlag, 1999, pages 187-196. Alternatively, the synthesis gas may be obtained by short contact time catalytic partial oxidation of hydrocarbonaceous feedstocks as described in EP 0303438. The synthesis gas can also be obtained via a 'compact reformer' process as described in Hydrocarbon Engineering, 2000, 5:5, 67-69; Hydrocarbon Processing, 2000, 79:9, 34; Today's Refinery, 2000, 15:8, 9; WO 9902254; and WO 0023689.

Typically, for commercial synthesis gas production the pressure at which the synthesis gas is produced from a steam reformer ranges from approximately 0.1 to 10 MPa, preferably 2 to 3 MPa and the temperatures at which the synthesis gas exits the reformer ranges from approximately 700 to 1000° C. Likewise, for commercial synthesis gas production the pressure at which the synthesis gas is produced from an auto-thermal reformer ranges from approximately 0.1 to 10 MPa, preferably 2 to 5 MPa and the temperatures at which the synthesis gas exits the reformer ranges from approximately 700 to 1300° C. Where the high temperatures are necessary in order to produce a favourable equilibrium for synthesis gas production, and to avoid metallurgy problems associated with carbon dusting. The synthesis gas contains a molar ratio of ($H_2$—$CO_2$):($CO$+$CO_2$) ranging from 0.8 to 3.0, which is dependent on the carbonaceous feedstock(s) and the method of reforming used. For example, when natural gas is used as the carbonaceous feedstock for steam reforming, the synthesis gas obtained usually has a maximum ($H_2$—$CO_2$):($CO$+$CO_2$) ratio of 3.0. However, when natural gas is used as the carbonaceous feedstock for auto-thermal reforming, the synthesis gas obtained usually has a ($H_2$—$CO_2$):($CO$+$CO_2$) ratio of 1.5.

According to a preferred embodiment of the present invention, the molar ratio, ($H_2$—$CO_2$):($CO$+$CO_2$), of the synthesis gas stream exiting the synthesis gas generation unit(s) is greater than 1.6, more preferably greater than 1.8 and most preferably greater than 2.0. Preferably, the molar ratio, ($H_2$—$CO_2$):($CO$+$CO_2$), of said synthesis gas stream exiting the synthesis gas generation unit(s) is less than 3.0, preferably less than 2.75, more preferably less than 2.4 and most preferably less than 2.2.

According to another embodiment of this invention when the carbonaceous feed stock used for synthesis gas generation is not an aliphatic hydrocarbon (e.g. coal, aromatic material, biomass) the molar ratio ($H_2$—$CO_2$):($CO$+$CO_2$) of the exit synthesis gas is preferably adjusted to the target value by addition of $H_2$ or removal of $CO_2$.

According to a preferred embodiment of the present invention, the exit stream obtained from the synthesis gas reactor (e.g. using a steam reformer), comprises essentially a mixture of carbon oxide(s) and $H_2$. It can also comprise water, nitrogen and traces of unconverted hydrocarbons (e.g. $C_1$-$C_3$ alkanes).

According to a preferred embodiment of the present invention, during synthesis gas generation, an additional stage may be employed whereby the feedstock is first purified to remove sulphur and other potential catalyst poisons (such as halides or metals e.g. mercury) prior to being converted into synthesis gas; alternatively this treatment can also be performed after synthesis gas preparation for example, when coal or biomass are used.

According to an embodiment of the present invention, at least part of the said synthesis gas stream is then introduced into a methanol synthesis unit, in order to produce a stream comprising methanol. Preferably the molar ratio, $(H_2—CO_2)$:$(CO+CO_2)$, of said synthesis gas feed stream fed into the methanol synthesis reactor is greater than 1.6, more preferably greater than 1.8 and most preferably greater than 2.0. Preferably the molar ratio, $(H_2—CO_2)$:$(CO+CO_2)$, of said synthesis gas feed stream fed into the methanol synthesis reactor is less than 3.0, more preferably less than 2.5 and most preferably less than 2.2.

According to a preferred embodiment of the present invention, the methanol synthesis unit may be any reactor that is suitable for producing methanol, for example a fixed bed reactor, which can be run in adiabatic or isothermal mode e.g. a multi-tubular reactor; or a fluidised bed reactor.

Preferably the methanol synthesis unit is operated at a temperature of more than 200° C., preferably more than 220° C. and most preferably more than 240° C.; and less than 310° C., preferably less than 300° C. and most preferably less than 290° C. Preferably the methanol synthesis unit is operated at pressure of more than 2 MPa and preferably more than 5 MPa; and less than 10 MPa and preferably less than 9 MPa. In fact, since methanol synthesis is an exothermic reaction, the chosen temperature of operation is governed by a balance of promoting the forward reaction (i.e. by not adversely affecting the equilibrium) and aiding the rate of conversion (i.e. higher productivity).

The catalysts used for methanol synthesis can be divided into 2 groups:
 i. the high pressure zinc catalysts, composed of zinc oxide and a promoter; and
 ii. low pressure copper catalysts, composed of zinc oxide, copper oxide and a promoter.

Hence, according to a preferred embodiment of the present invention, the preferred methanol synthesis catalyst is a mixture of copper, zinc oxide, and a promoter such as, chromia or alumina. Under the aforementioned operating conditions, these said mixtures can catalyse the production of methanol from CO and $H_2$ with a high selectivity.

Additionally by-products such as methane, ethanol and other higher alcohols may also be produced during methanol synthesis. According to a preferred embodiment of this aspect of the present invention, the stream exiting the methanol synthesis reactor is subsequently purified to remove said by-products by any methods known to those skilled in the art.

According to another aspect of the present invention, a methanol stream, together with a substantially pure CO stream, are introduced into a carbonylation reactor. Preferably, at least part of the said methanol stream emanates from the aforementioned methanol synthesis unit, however said methanol stream may also emanate from another suitable source, such as a bio-fermentation process and/or pyrolysis (e.g. wood pyrolysis).

Preferably at least a part of the said CO stream is obtained from the aforementioned synthesis gas generation stage. This is preferably performed by first removing $CO_2$ and water from the generated synthesis gas followed by a cryogenic separation to isolate the substantially pure CO from the $H_2$. Alternative methods of separation, such as membrane separation technologies can also be employed. Alternatively, said CO stream may also be obtained from another suitable source, such as another chemical process (e.g. off-gas from steel manufacture). Said CO stream(s) may still contain inert impurities such as $CO_2$, methane, nitrogen, noble gases, water and $C_1$ to $C_4$ paraffinic hydrocarbons, which are preferably removed before use.

According to this aspect of the present invention, the step of introducing methanol, together with CO, into a carbonylation reactor is performed under conditions favourable for producing ethanoic acid.

There are many examples in the prior art which disclose carbonylation processes that can be suitably used in the present invention.

For example, such carbonylation processes can be made in the presence of iridium catalysts as described in U.S. Pat. No. 3,772,380. UK patent GB 1276326 also describes the preparation of mono-carboxylic, acids by carbonylation of alcohols in the presence of rhodium or iridium catalysts, halogen promoters and water or an alcohol, ether or ester.

Carbonylation processes in the presence of ruthenium and osmium catalysts can also be suitably used in the present invention. Thus, UK patents GB 1234641 and GB 1234642 describe a process for the production of an organic acid by carbonylation of an alcohol in the presence of a noble metal catalyst selected from iridium, platinum, palladium, osmium and ruthenium and their compounds and a promoter which is halogen or halogen compound. According to Jenner et al, Journal of Molecular Catalysis, 1987, 40, 71-82 ruthenium compounds are effective carbonylation catalysts for converting primary alcohols into acids at high CO pressures. Standard conditions of 45 MPa CO pressure were used in the reported experiments. For example, UK patent application GB 2029409 describes a process for the preparation of aliphatic carboxylic acids by reacting CO with alcohols at an elevated pressure of 3.4 MPa or greater in the presence of a ruthenium catalyst and halogen-containing promoter.

According to a preferred embodiment of this aspect of the present invention, the carbonylation process takes place in the presence of an iridium catalyst together with at least one promoter; indeed, such catalyst systems have proven to have beneficial effects on the rate of carbonylation of methanol. Said carbonylation process is thus preferably performed in the presence of at least a finite concentration of water with a catalyst system comprising:
(a) an iridium catalyst, (b) methyl iodide and (c) at least one promoter.

Thus, according to a preferred embodiment of this aspect of the present invention the process for the production of ethanoic acid by carbonylation of methanol comprises contacting methanol with CO, in the liquid reaction composition, in a carbonylation reactor wherein, the liquid reaction composition comprises:
(a) ethanoic acid, (b) an iridium catalyst, (c) methyl iodide, (d) water and (e) at least one promoter.

According to an embodiment of this aspect of the present invention, during the carbonylation process, water may be formed in situ in the liquid reaction composition. For example, water may be produced via by-product formation, generated during methane production. Water may also be generated during the esterification reaction between methanol reactant and ethanoic acid product. Water may also be introduced to the carbonylation reactor together with, or separately from, other components of the liquid reaction composition. Water may be separated from other components of reaction composition withdrawn from the reactor and may be recycled in controlled amounts to maintain a preferred concentration of water in the liquid reaction composition. Preferably, the concentration of water in the liquid reaction composition of the carbonylation reactor is in the range 0.1 to 15 wt %; more preferably 1 to 10 wt %, most preferably 1 to 6.5 wt %.

The iridium catalyst in the liquid reaction composition may comprise any iridium containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium ethanoate, $[Ir_3O(OAc)_6(H_2O)_3][OAc]$, and hexachloroiridic acid $[H_2IrCl_6]$, preferably, chloride-free complexes of iridium such as ethanoates, oxalates and acetoacetates which are soluble in one or more of the carbonylation reaction components such as water, alcohol and/or carboxylic acid. Particularly preferred is green iridium ethanoate which may be used in an ethanoic acid or aqueous ethanoic acid solution.

Preferably, the iridium carbonylation catalyst concentration in the liquid reaction composition is in the range 100 to 6000 ppm by weight of iridium, more preferably 700 to 3000 ppm by weight of iridium.

In the process of the present invention at least one promoter is present in the reaction composition. Suitable promoters are preferably selected from the group consisting of ruthenium, osmium, rhenium, cadmium, mercury, zinc, gallium, indium and tungsten, and are more preferably selected from ruthenium and osmium and most preferably is ruthenium. Preferably, the promoter is present in an effective amount up to the limit of its solubility in the liquid reaction composition and/or any liquid process streams recycled to the carbonylation reactor from the ethanoic acid recovery stage. The promoter is suitably present in the liquid reaction composition at a molar ratio of promoter:iridium of [0.5 to 15]:1. As noted above, the beneficial effect of a promoter such as ruthenium has been found to be greatest at the water concentration which gives the maximum carbonylation rate at any defined methyl ethanoate and methyl iodide concentration. A suitable promoter concentration is 400 to 5000 ppm by weight.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) methanoate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium (II,III), ruthenium (III) ethanoate, ruthenium (III) propanoate, ruthenium (III) butanoate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1,5-diene)ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[O_s(CO)_4I_2]$, $[Os(CO)_3I_2]_2$, $[Os(CO)_3I_3]^-H^+$, pentachloro-mu-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $[Re(CO)_4I_2]^-H^+$, and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$, and zinc acetylacetonate.

Examples of suitable gallium-containing compounds which may be used as sources of promoter include gallium acetylacetonate, gallium ethanoate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium ethanoate, $InCl_3$, $InBr_3$, $InI_3$, $InI$ and $In(OH)_3$.

Examples of suitable tungsten-containing compounds which may be used as sources of promoter include $W(CO)_6$, $WCl_4$, $WCl_6$, $WBr_5$, $WI_2$, or $C_9H_{12}W(CO)_3$ and any tungsten chloro-, bromo- or iodo-carbonyl compound.

Preferably, the iridium- and promoter-containing compounds are free of impurities which provide or generate in situ ionic iodides which may inhibit the reaction, for example, alkali or alkaline earth metal or other metal salts.

Ionic contaminants such as, for example, (a) corrosion metals, particularly nickel, iron and chromium and (b) phosphines or nitrogen containing compounds or ligands which may quaternise in situ; should be kept to a minimum in the liquid reaction composition as these will have an adverse effect on the reaction by generating $I^-$ in the liquid reaction composition which has an adverse effect on the reaction rate. Some corrosion metal contaminants such as for example molybdenum have been found to be less susceptible to the generation of $I^-$. Corrosion metals which have an adverse affect on the reaction rate may be minimised by using suitable corrosion-resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate 500 ppm by weight of $I^-$, preferably less than 250 ppm by weight of $I^-$ in the liquid reaction composition.

Preferably, the concentration of methyl iodide in the liquid reaction composition is in the range 1 to 20 wt %, preferably 5 to 16 wt %.

The partial pressure of CO in the carbonylation reactor is suitably in the range 0.1 to 7 MPa preferably 0.1 to 3.5 MPa and most preferably 0.1 to 1.5 MPa.

The presence of $H_2$ in the CO fed and generated in situ by the water-gas shift reaction is preferably kept low as its presence may result in the formation of hydrogenation products. Thus, the ratio of $H_2$ to CO reactant is preferably less than 0.01:1, more preferably less than 0.005:1 and yet more preferably less than 0.003:1 and/or the partial pressure of $H_2$ in the carbonylation reactor is preferably less than 0.1 MPa, more preferably less than 0.05 MPa and yet more preferably less than 0.03 MPa.

The catalyst system used in the carbonylation process of the present invention has been found to be particularly beneficial at relatively low partial pressures of CO where the rate of reaction may be dependent upon the CO partial pressure. Under these conditions, it has been found that the catalyst system has the advantage of providing an increased rate of reaction over catalyst systems without the promoters of the present invention. This advantage allows for an increased rate of reaction under conditions when the CO partial pressure is relatively low, for example due to a low total pressure in the carbonylation reactor or due to high vapour pressure of components of the liquid reaction composition, e.g. at high methyl ethanoate concentration in the liquid reaction composition or due to a high concentration of inert gases (for example nitrogen and $CO_2$) in the carbonylation reactor. The catalyst system may also have advantages of increasing rate of carbonylation when the rate of reaction is reduced by the availability of CO in solution in the liquid reaction composition resulting from mass transfer limitations, for example due to poor agitation.

The pressure of the carbonylation reaction is suitably in the range 0.9 to 19.9 MPa, preferably 0.9 to 9.9 MPa, most preferably 1.4 to 4.9 MPa. The temperature of the carbonylation reaction is suitably in the range 100 to 300° C., preferably in the range 150 to 220° C.

Ethanoic acid may advantageously be used as a solvent for said carbonylation reaction.

The carbonylation process of the present invention may be performed as a batch or continuous process, preferably as a continuous process and may be performed in any suitable reactor, known to those skilled in the art.

The ethanoic acid product may be removed from the reactor by withdrawing liquid reaction composition and separating the ethanoic acid product by one or more flash and/or fractional distillation stages from the other components of the liquid reaction composition such as iridium catalyst, ruthenium and/or osmium and/or indium promoter, methyl iodide, water and unconsumed reactants which may be recycled to the reactor to maintain their concentrations in the liquid reaction composition. The ethanoic acid product may also be removed as a vapour from the stream exiting the carbonylation reactor.

Although halide promoters and stabilizers, such as methyl iodide, improve the efficiency and productivity of carbonylation processes, the continued presence of halide compounds in the carbonylation reaction products is undesirable if the product is employed as a starting material in a subsequent process employing a halide-sensitive catalyst where poisoning effects may be cumulative and irreversible. In a preferred embodiment the ethanoic acid product is purified of halide compounds. This purification treatment can be achieved by any appropriate method known to those skilled in the art. For example halides can be removed from the liquid phase using silver salts either unsupported, or supported, on an ion-exchange resin or a zeolite as exemplified in U.S. Pat. No. 5,344,976 and references therein According to the present invention, ethanoic acid is introduced into a primary hydrogenation unit together with $H_2$ to produce a stream comprising ethyl ethanoate and ethanol in the presence of a precious metal-based catalyst. In addition to the production of ethanol and ethyl ethanoate, the primary hydrogenation process also produces water, other reaction products (e.g. trace amounts of methane, ethane, diethyl ether and ethanal) and unreacted reactants (e.g. ethanoic acid and $H_2$).

The proportion of ethyl ethanoate present in the exit stream of the primary hydrogenation unit will be determined by the nature of the catalyst, process conditions, and the degree of conversion. The proportion of ethyl ethanoate may be further increased, if desired, by introducing an acidic function into the catalyst to promote in situ esterification.

It is preferable according to the present invention to operate at medium or high conversion of ethanoic acid to ester and alcohol, preferably at more than 50% and less than 90% and most preferably more than 60% and less than 80% conversion per pass.

According to an embodiment of the present invention, at least a part of the ethanoic acid introduced into the primary hydrogenation unit emanates from the aforementioned carbonylation reactor. However, in practice, the said ethanoic acid may originate from another suitable source, such as wood pyrolysis and/or as a by-product of a fermentation process to produce alcohol(s).

Preferably, at least a part of the $H_2$ introduced into the primary hydrogenation unit emanates from the synthesis gas generation procedure (i.e. it is obtained during the aforementioned $CO/H_2$ separation), where, if need be, the $H_2$ content can be further increased by subjecting the said synthesis gas to a water-gas shift reaction and a subsequent $H_2$ separation.

Alternatively the $H_2$ introduced into the primary hydrogenation unit may originate from a variety of other chemical processes, including ethene crackers, styrene manufacture and catalytic reforming. However, it is known that the main commercial processes for purposeful generation of $H_2$ are autothermal reforming, steam reforming and partial oxidation of carbonaceous feedstocks such as natural gas, coal, coke, deasphalter bottoms, refinery residues and biomass. $H_2$ may also be produced by electrolysis of water.

The overall choice of technology for producing $H_2$ is generally determined by the following economic considerations and factors:
  i. feedstock cost
  ii. feedstock availability
  iii. capital cost
  iv. local energy and operating costs; and
  v. environmental considerations According to an embodiment of the present invention, the resulting stream from the primary hydrogenation unit can be fed directly into a secondary hydrogenation unit, together with an optional source of $H_2$. Whereby preferably, at least a part of said optional $H_2$ that is introduced into the secondary hydrogenation unit, is sourced from the same feedstock as the $H_2$ that is introduced into the primary hydrogenation unit; or is alternatively obtained from any of the aforementioned processes.

According to a preferred embodiment of the present invention, at least 50%, preferably at least 75%, more preferably at least 90% and most preferably at least 95% of the ethyl ethanoate introduced into the secondary hydrogenation unit is converted per pass.

Indeed, the applicants have found that by using a proportion of the synthesis gas generated for the aforementioned methanol synthesis stage for the source of CO used in the carbonylation reactor and as a source of $H_2$ used for both of the hydrogenation units, an economy on scale on synthesis gas generation could be achieved, as well as achieving a reduction in greenhouse gas emissions.

An advantage of this two-step hydrogenation process has been found, in that the selectivity of the ethanoic acid hydrogenation to ethanol can be further increased at the expense of undesirable by-products, such as the aforementioned alkanes (e.g. ethane and methane).

The catalyst employed in the primary hydrogenation unit is a precious metal-based catalyst, preferably comprising of at least one noble metal from Group VIII of the periodic table (CAS version, for example ruthenium, osmium, cobalt, rhodium, iridium, nickel, palladium, platinum) and at least one of the metals chosen from rhenium, silver, tungsten and/or molybdenum; and optionally an additional metal, that is capable of alloying with said Group VIII noble metal. Preferably the catalyst employed in the primary hydrogenation reactor is a palladium based catalyst. Whereby the preferred palladium based catalyst is a supported catalyst which comprises palladium and preferably rhenium and/or silver. Additional promoters such as Fe can also advantageously be used.

The catalyst employed in the secondary hydrogenation unit is a copper-based catalyst (for example a copper chromite or a mixed copper metal oxide based catalyst wherein the second metal can be copper, zinc, zirconium or manganese).

According to a preferred embodiment of the present inventions the catalyst(s) employed in the secondary hydrogenation unit is a copper-based catalyst more preferably comprising copper and zinc, most preferably consisting of copper-zinc-oxide.

All of the aforementioned catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. Preferably, the copper-based catalyst is supported on zinc oxide and preferably comprises between 20 and 40 wt % of copper.

One or both of the hydrogenation processes (i.e. primary and secondary hydrogenations) may be operated in a gas phase mode, or alternatively in a gas/liquid phase mode (e.g. a trickle bed or a bubble reactor). The gas/liquid phase regime is where the reactant mixture at the reactor conditions is below the dewpoint temperature. Preferably, the secondary hydrogenation reaction is conducted in a gas phase regime. The hydrogenation can be conducted in batch or semi-continuous or continuous mode. Continuous mode of operation is the most preferred.

The catalyst employed in either hydrogenation reaction may be homogeneous (liquid/gas phase only) or heterogeneous; with heterogeneous catalysts being preferred.

One or both of the hydrogenation processes can be conducted in adiabatic and/or isothermal reactors; where adiabatic mode of operation is preferred. Suitable reactors for a gas phase reaction include single or a plurality of adiabatic bed reactors which can be used in series or in parallel. For reactors utilised in series, heat exchangers and/or intercoolers and/or additional reactant and/or recycle of intermediates can be employed in between successive reactors to control the reaction temperature. In both primary and secondary hydrogenation reactions, the preferred adiabatic temperature rise is less than 50° C., preferably less than 25° C. and most preferably less than 10° C. The preferred use of adiabatic reactors is in series. To one skilled in the art, production of ethanol in large quantities may require several parallel trains of series of adiabatic reactors. The adiabatic reactors may be operated at different temperatures depending on the composition of the individual reactor feeds.

Gas phase hydrogenations can also be conducted in multi-tubular reactors in which case the tubes separate a reaction section from a cooling/heating medium which controls the reaction temperature. For exothermic reactions, such as ethanoic acid hydrogenation this results in a radial temperature gradient in the reactor, the preferred gradient is less than 50° C. preferably less than 25° C. most preferably less than 10° C. The preferred flow regime in this type of reactor is turbulent rather than laminar; this corresponds to a Reynolds number (of the flowing fluid) that is greater than 2100 (where the gas velocity is approximated by the gas velocity in an unpacked tube).

The gas phase hydrogenation reaction(s) can also be conducted in other reactor types such as fluidised bed, spinning basket, buss loop and heat exchanger reactors.

A mixed gas/liquid phase hydrogenation reaction(s) can be conducted with co-flow or counterflow $H_2$ and gas to the liquid (e.g. a bubble reactor). The preferred mode of operation of gas/liquid reactors is co-flow, also known as trickle bed operation; this can be conducted in at least one tubular and/or multi-tubular reactor in series. The hydrogenation reaction(s) may change from a mixed gas/liquid phase to a fully gas phase reaction, as the reaction proceeds down the reactor, due to changes in composition, temperature, and pressure. The mixed phase hydrogenation can also be conducted in other types of reactors, or a combination of different reactors, for example in a slurry or stirred tank reactor with, or without, external circulation and optionally operated as a cascade or stirred tanks, a loop reactor or a Sulzer mixer-reactor.

Both the primary and secondary hydrogenation reactions may be operated at a temperature of between 150° C. and 290° C.

According to a preferred embodiment of the present invention, the reaction temperature of the primary hydrogenation unit (e.g. using a palladium-based catalyst) is more than 180° C., preferably more than 200° C. and most preferably more than 210° C.; and less than 290° C., preferably less than 270° C. and most preferably less than 250° C.

According to another embodiment of the present invention the reaction temperature of the secondary reactor (e.g. using a copper-based catalyst) is more than 150° C., preferably more than 170° C. and most preferably more than 190° C.; and less than 250° C.

Both the primary and secondary hydrogenation reactions may be operated at a pressure of more than 3 MPa, preferably at a pressure of more than 5 MPa; and at a pressure of less than 15 MPa, more preferably at a pressure less than 13 MPa and most preferably at a pressure less than 9 MPa.

If either of the hydrogenation reactions are conducted in the gas phase, then the GHSV, for continuous operation may be in the range of 50 to 50,000 $h^{-1}$, preferably from 1,000 to 30,000 $h^{-1}$ and most preferably from 2,000 to 9,000 $h^{-1}$.

The liquid substrate introduced into the hydrogenation unit preferably has a LHSV which may be less than 10 $h^{-1}$, more preferably less than 5 $h^{-1}$ and most preferably less than 3 $h^{-1}$; for example, a typical LHSV for normal operation is approximately 1 $h^{-1}$.

In practice, the conditions employed in either the primary hydrogenation unit, or the secondary hydrogenation unit, are chosen in order to favour the overall selectivity to ethanol, given the composition of the initial feedstock (e.g. a feedstock comprising ethanoic acid and $H_2$ in the case of the primary hydrogenation unit; and, a feedstock comprising ethyl ethanoate and $H_2$ in the secondary hydrogenation unit).

However, the applicants have found that when the relationship of the process conditions between the two is such that the second hydrogenation unit is preferably operated at a temperature of at least 10° C., more preferably at least 20° C., lower than the operating temperature of the first hydrogenation unit, they were able to obtain an unexpectedly high selectivity towards ethanol whilst achieving high conversion of the ethanoic acid.

According to an embodiment of the present invention, at least a part of the stream exiting the secondary hydrogenation unit is passed through a separation unit (e.g. a separation column), to give streams which may include a stream comprising ethyl ethanoate, a stream comprising ethanoic acid and a stream comprising ethanol.

According to an embodiment of the present invention, at least a part of the stream exiting the second hydrogenation unit is also passed through a separation unit (e.g. a separation column)—which may be the same or preferably different from the above separation unit to give streams which may include a stream comprising ethyl ethanoate, a stream comprising ethanoic acid and a stream comprising ethanol.

Preferably, the separated stream comprising ethanoic acid from the first hydrogenation unit (preferably together with the stream comprising ethanoic acid from the second hydrogenation unit) is recovered and recycled back into the primary hydrogenation unit.

The separated stream comprising ethyl ethanoate from the first hydrogenation unit (preferably together with the stream comprising ethyl ethanoate from the second hydrogenation unit) is recovered and introduced into the second hydrogenation unit.

The Applicants have also discovered another additional embodiment according to the present invention whereby an ethanol/ethyl ethanoate mixture is also advantageously separated from the stream exiting either the first or the second or preferably both hydrogenation units, and is then fed into the second hydrogenation unit.

Additionally water is advantageously separated from the stream exiting the first hydrogenation unit in order to maintain an anhydrous feed to the second hydrogenation unit. Preferably this separation is performed in a distillation column with butyl acetate. According to this embodiment the total feed introduced into the second hydrogenation unit contains less than 10 wt %, preferably less than 5 wt. % and most preferably less than 1 wt % water.

Furthermore, any unreacted $H_2$ present in the exit stream of the primary hydrogenation unit and/or the secondary hydrogenation unit is preferably separated and may advantageously be recycled into either the primary hydrogenation unit and/or the secondary hydrogenation unit.

Optionally, at least a part of the ethanol present in the exit stream of the primary hydrogenation unit is separated and recovered as the desired product together with the ethanol obtained from the secondary hydrogenation unit.

By performing these embodiments the applicants were able to achieve an even higher selectivity towards ethanol for a given ethanoic acid and/or ethyl ethanoate to ethanol conversion than from a single reactor in which ethanoic acid is hydrogenated and without the expense of an esterification unit to generate ethyl ethanoate for a reactor in which ethyl ethanoate is hydrogenated. High conversion in the secondary hydrogenation unit (>70%) is favoured as it unexpectedly simplifies the isolation of the ethanol product. In addition to this high selectivity is also desirable as it reduces the amount of water generated as a reaction by-product, and high selectivities >90% reduce the impact of water azeotropes on the separation.

The separation step may be performed by any means known to those skilled in the art that is suitable for separating the said stream(s), e.g. a sieve tray column, a packed column, a bubble cap column or a combination thereof.

According to a preferred embodiment of the present invention, the molar ratio of $H_2$ to ethanoic acid that is introduced into the primary hydrogenation unit is greater than 2:1, preferably the molar ratio is greater than 4:1 and most preferably the molar ratio is greater than 5:1; and is less than 100:1, preferably less than 50:1 and most preferably less than 15:1.

According to a preferred embodiment of the present invention, the molar ratio of $H_2$ to [ethyl ethanoate and ethanoic acid] that is introduced into the secondary hydrogenation unit is greater than 2:1, preferably the molar ratio is greater than 4:1 and most preferably the molar ratio is greater than 5:1; and is less than 100:1, preferably less than 50:1 and most preferably less than 15:1.

It should be noted that whilst all of the aforementioned temperature and pressure operating conditions form preferred embodiments of the present invention, they are not, by any means, intended to be limiting, and the present invention hereby includes any other pressure and temperature operating conditions that achieve the same effect.

Figure 2:
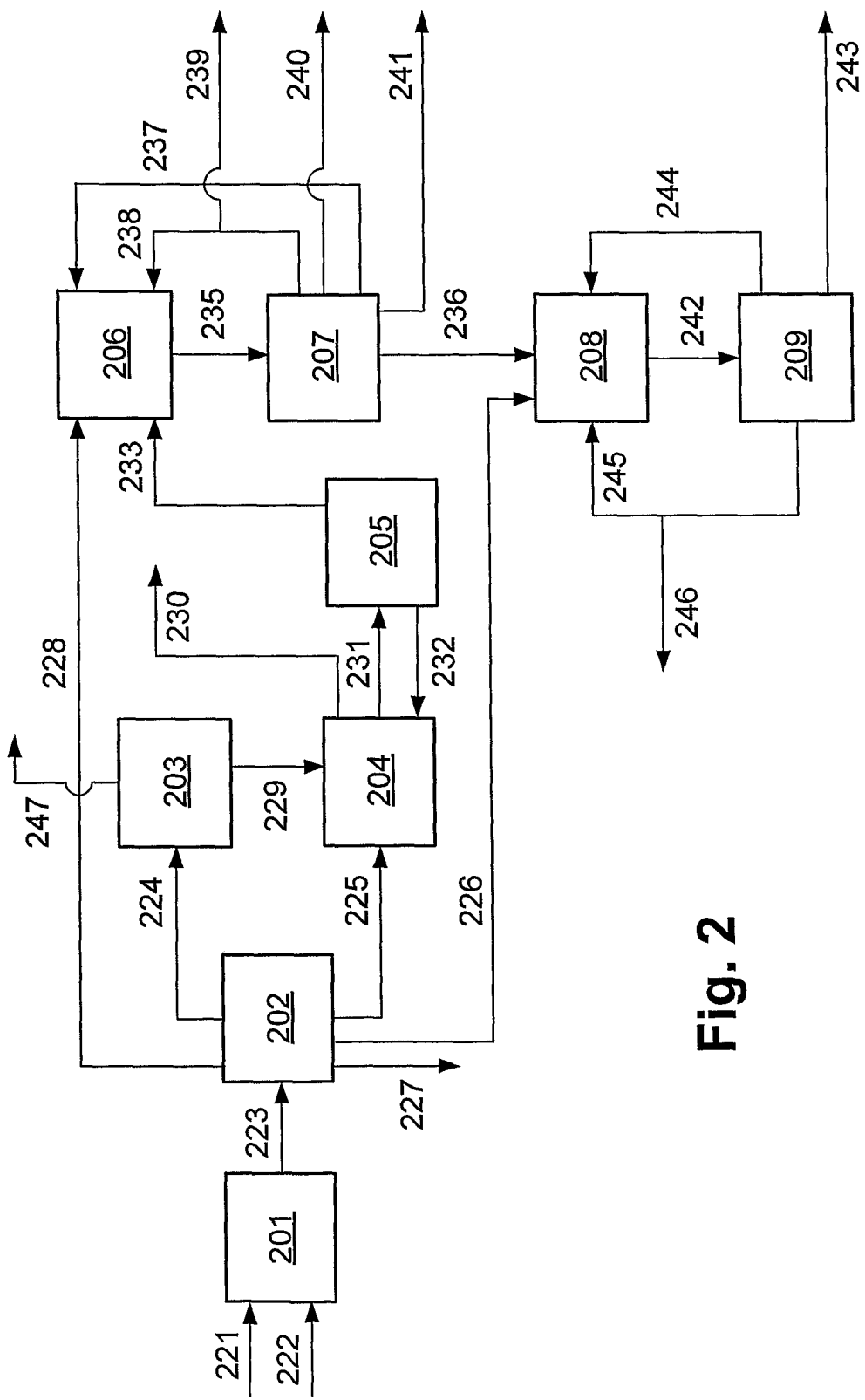

FIG. 2, is a simplified flow diagram of an embodiment of this invention and a process for the production of ethanol from a carbonaceous feedstock is shown. A carbonaceous feedstock stream is supplied to the synthesis gas generation unit, 201, through line 221 and a stream comprising water and/or oxygen is supplied to the synthesis gas generation unit through line 222. Synthesis gas from the synthesis gas generation unit is passed to a synthesis gas separation zone, 302, through line 223. In the synthesis gas separation zone crude synthesis gas from the synthesis gas generation zone is separated to provide synthesis gas as well as CO and $H_2$ streams. Water is removed from the synthesis gas separation unit through line 227. Synthesis gas from the synthesis gas separation zone is fed to the methanol synthesis zone, 303, through line 224. In the methanol synthesis zone synthesis gas is converted to methanol in a methanol synthesis reactor and methanol is separated from the methanol synthesis reactor product stream. A purge stream is taken from the methanol synthesis zone through line 247 to control the build up of diluent gases in the methanol synthesis zone. Methanol is fed from the methanol synthesis zone to the carbonylation reactor, 304, through line 227. CO from the synthesis gas separation zone is fed to the carbonylation reactor through line 225. Methanol and CO are reacted together in the carbonylation reactor in a liquid reaction composition which comprises ethanoic acid, an iridium catalyst, methyl iodide, water and at least one promoter. A purge stream is taken from the carbonylation reactor through line 230 to control the build up of diluent gases in the carbonylation reactor. The liquid reaction composition from the carbonylation reactor is passed to an ethanoic acid separation and purification zone, 205, through line 231. Ethanoic acid is separated from the carbonylation reaction liquid reaction composition in the ethanoic acid separation and purification zone. A stream comprising the iridium catalyst, methyl iodide, water and promoter is returned to the carbonylation reactor from the ethanoic acid separation and purification zone through line 232. Ethanoic acid is further purified of halide compounds in the ethanoic acid separation and purification zone. Ethanoic acid is fed from the ethanoic acid separation and purification zone to the primary hydrogenation reactor, 206, through line 233. $H_2$ from the synthesis gas separation zone is fed to the primary hydrogenation reactor through line 228. The primary hydrogenation reactor contains a solid hydrogenation catalyst and the reactor is maintained at conditions of temperature and pressure such that a gas phase reaction takes place. Ethanoic acid and $H_2$ are converted in the primary hydrogenation reactor to a mixture comprising ethanoic acid, ethyl ethanoate, ethanol, water and $H_2$ which is passed to the first hydrogenation separation zone, 207, through line 235. In the primary hydrogenation separation zone ethanoic acid is separated and passed back to the primary hydrogenation reactor through line 237 and water is separated and passed from the process through line 241. A gas stream comprising $H_2$ is separated in the primary hydrogenation separation zone and passed back to the primary hydrogenation reactor through line 238. A purge stream is taken from this gas recycle stream through line 239 to control the build up of diluent gases in the primary hydrogenation reactor. A first product ethanol stream is taken from the process from the primary hydrogenation separation zone through line 240. Ethyl ethanoate from the primary hydrogenation separation zone is passed to the secondary hydrogenation reactor, 208, through line 236. $H_2$ from the synthesis gas separation zone is fed to the secondary hydrogenation reactor through line 226. The secondary hydrogenation reactor contains a solid hydrogenation catalyst and the reactor is maintained at conditions of temperature and pressure such that a gas phase reaction takes place. Ethyl ethanoate and $H_2$ are converted in the secondary hydrogenation reactor to a mixture comprising ethanol, ethyl ethanoate and $H_2$, which is passed to the secondary hydrogenation separation zone, 209, through line 242. In the secondary hydrogenation separation zone ethyl ethanoate is separated and passed back to the secondary hydrogenation reactor through line 244. A gas stream comprising $H_2$ is separated in the secondary hydrogenation separation zone and passed back to the secondary hydrogenation reactor through line 245. A purge stream is taken from this gas recycle stream through line 246 to control the build up of diluent gases in the secondary hydrogenation reactor. A second product ethanol stream is taken from the process from the secondary hydrogenation separation zone through line 243.

EXAMPLES

The example describes the hydrogenation, in a primary reactor, of ethanoic acid to ethyl ethanoate over a palladium-silver-rhenium-iron catalyst followed by the hydrogenation, in a secondary reactor, of ethyl ethanoate to ethanol over a copper-based catalyst. The comparative example describes the hydrogenation, in a primary reactor, of ethanoic acid to ethyl ethanoate over a palladium-silver-rhenium-iron catalyst and the hydrogenation, in a secondary reactor, of ethyl ethanoate to ethanol over the same palladium-silver-rhenium-iron catalyst.

Catalysts

The catalysts used for the example and comparative example were as follows. The palladium-silver-rhenium-iron supported on carbon extrudate Norit RX3 catalyst used in the example and the comparative example was prepared as described in U.S. Pat. No. 5,969,164. The composition of the catalyst was: 2.6 wt % palladium; 6.7 wt % rhenium; 1.7 wt % silver; and, 0.69 wt % iron. The copper-based catalyst used in the example was T-2130 supplied by Sud-Chemie. The composition was CuO 33 wt %, ZnO 66 wt %.

Catalyst Testing

The examples were carried out in pressure flow reactors

In the primary reactor the palladium-silver-rhenium-iron catalyst was activated by heating to 100° C. under a flow of nitrogen at approximately 0.25 MPa and a GHSV of 1500 $h^{-1}$. The concentration of $H_2$ in nitrogen was increased in stages to 10, 20, 40, 70 and 100 mol % with 1 h dwell time at each stage. The catalyst was then heated at 1° C./min to a holding temperature of 250° C. and was held for a dwell time of 3 h. At this point catalyst activation was considered complete.

In the secondary reactor the copper-based catalyst was activated by heating to 100° C. under a flow of 5 mol % $H_2$ in nitrogen at 2.5 MPa and a GHSV of 6000 $h^{-1}$. The concentration of $H_2$ was increased in stages to 10, 20, 40, 70 and 100 mol % with 1 h dwell time at each stage. The catalyst was then heated at 1° C./min to a holding temperature of 180° C. and held for a dwell time of 24 h.

In the secondary reactor the palladium-silver-rhenium-iron catalyst was activated by heating to 100° C. under a flow of 5 mol % $H_2$ in $N_2$ at 3.0 MPa and a GHSV of 6000 $h^{-1}$. The concentration of $H_2$ was then increased in stages to 25, 50, 75 and 100 mol % with a 1 h dwell time at each stage. The catalyst was heated at 1° C./min to a holding temperature of 250° C. and was held for a dwell time of 1 h.

Example

In the primary reactor $H_2$ and ethanoic acid with a molar ratio of 10:1 was passed over the palladium-silver-rhenium-iron catalyst at 230° C. and 2.0 MPa with a GHSV of 4343 $h^{-1}$. The conversion of ethanoic acid to ethyl groups recoverable as ethanol was 41.9% of which 19.7% was as ethyl ethanoate, 21.6% ethanol, 0.4% ethanal and 0.2% diethyl ether and the total conversion of ethanoic acid to products was 44.7%. The selectivity of ethanoic acid to ethyl groups recoverable as ethanol was 93.8%

In the secondary reactor $H_2$ and ethyl ethanoate with a molar ratio of 10:1 was passed over the copper-based catalyst at 200° C. and 5.0 MPa with a GHSV of 4491 $h^{-1}$. The conversion of ethyl ethanoate to ethyl groups recoverable as ethanol was 69.5%. The selectivity of ethyl ethanoate to ethyl groups recoverable as ethanol was 99.9%. By operating the secondary reactor to hydrogenate all the ethyl ethanoate of the first reactor at this selectivity the total conversion of ethanoic acid to all products across the two reactors was 64.4%. The selectivity of ethanoic acid to ethyl groups recoverable as ethanol from the two reactors was 95.7%, that is to say an overall loss of selectivity across the two reactors of 4.3%

Comparative Example

The hydrogenation of ethanoic acid to give ethyl ethanoate was carried out in the primary reactor as in the example above.

In the secondary reactor $H_2$ and ethyl ethanoate with a molar ratio of 10:1 was passed over the palladium-silver-rhenium-iron catalyst at 225° C. and 5.0 MPa with a GHSV of 3722 $h^{-1}$. The conversion of ethyl ethanoate to ethyl groups recoverable as ethanol was 57.2%. The selectivity of ethyl ethanoate to ethyl groups recoverable as ethanol was 92.8%. By operating the second reactor to hydrogenate all the ethyl ethanoate of the first reactor at this selectivity the total conversion of ethanoic acid to all products across the two reactors was 64.4%. The selectivity of ethanoic acid to ethyl groups recoverable as ethanol from the two reactors was 91.3%, that is to say an overall loss of selectivity across the two reactors of 8.7%.

The invention claimed is:
1. Process for the conversion of ethanoic acid into ethanol comprising the following steps:
    (a) introducing ethanoic acid and $H_2$ into a primary hydrogenation unit in the presence of a precious metal-based catalyst to produce ethanol and ethyl ethanoate,
    (b) introducing ethyl ethanoate, from step (a), together with $H_2$ into a secondary hydrogenation unit in the presence of a copper-based catalyst to produce ethanol, and
    (c) recovering ethanol from step (b).

2. A process for the conversion of methanol into ethanol, comprising the following steps:
  (a) introducing methanol, together with CO, into a carbonylation reactor to produce ethanoic acid,
  (b) introducing ethanoic acid, from step (a), together with $H_2$, into a primary hydrogenation unit in the presence of a precious metal-based catalyst to produce ethanol and ethyl ethanoate,
  (c) introducing ethyl ethanoate from step (b), together with $H_2$, into a secondary hydrogenation unit in the presence of a copper-based catalyst to produce ethanol, and
  (d) recovering ethanol from step (c).

3. Process for the conversion of a carbonaceous feedstock into ethanol, whereby the carbonaceous feedstock is first converted into synthesis gas, which is subsequently converted into ethanol, comprising the following consecutive steps:
  (a) introducing a carbonaceous feedstock into a synthesis gas generation unit to produce synthesis gas,
  (b) introducing synthesis gas, produced in step (a), into a methanol synthesis reactor to produce methanol,
  (c) introducing methanol from step (b), together with CO, into a carbonylation reactor to produce ethanoic acid,
  (d) introducing ethanoic acid, from step (c), together with $H_2$, into a primary hydrogenation unit in the presence of a precious metal-based catalyst to produce ethanol and ethyl ethanoate,
  (e) introducing ethyl ethanoate, from step (d), together with $H_2$, into a secondary hydrogenation unit in the presence of a copper-based catalyst to produce ethanol, and
  (f) recovering ethanol from step (e).

4. Process according to claim 2, wherein the step of producing ethanoic acid by carbonylation of methanol comprises contacting methanol with CO, in the liquid reaction composition, in a carbonylation reactor, wherein the liquid reaction composition comprises:
  (a) ethanoic acid,
  (b) an iridium catalyst,
  (c) methyl iodide,
  (d) water, and
  (e) a promoter.

5. Process according to claim 4, wherein the promoter is selected from ruthenium and osmium.

6. Process according to claim 5, wherein the concentration of water in the liquid reaction composition of the carbonylation reactor is in the range 0.1 to 15 wt %.

7. Process according to claim 1, wherein the precious metal-based catalyst is a supported catalyst which comprises palladium.

8. Process according to claim 1, wherein the secondary hydrogenation unit is operated in a gas phase regime.

9. Process according to claim 1, wherein the secondary hydrogenation unit is operated at a temperature of at least 10° C. lower than the operating temperature of the primary hydrogenation unit.

10. Process according to claim 1, wherein more than 50% and less than 90% of the ethanoic acid introduced into the primary hydrogenation unit is converted into ethanol and ethyl ethanoate per pass.

11. Process according to claim 1, wherein at least 50% of the ethyl ethanoate introduced into the secondary hydrogenation unit is converted into ethanol per pass.

12. Process according to claim 1, wherein the stream exiting the secondary hydrogenation unit, which stream comprises ethanol, ethanoic acid, ethyl ethanoate and $H_2$, is passed through a separation unit, and wherein the separated ethanoic acid is recycled to the primary hydrogenation unit and the separated ethyl ethanoate is introduced into the secondary hydrogenation unit.

13. Process according to claim 1, wherein the stream exiting the primary hydrogenation unit, which stream comprises ethanol, ethanoic acid, ethyl ethanoate and $H_2$, is passed through a separation unit, and the separated ethyl ethanoate is introduced into the secondary hydrogenation unit.

14. Process according to claim 12, wherein the separated $H_2$ is recycled into either the primary hydrogenation unit and/or the secondary hydrogenation unit.

15. Process according to claim 1, wherein the molar ratio of $H_2$ to ethanoic acid that is introduced into the primary hydrogenation unit is greater than 2:1 and is less than 100:1.

16. Process according to claim 1, wherein the molar ratio of $H_2$ to [ethyl ethanoate and ethanoic acid] that is introduced into the secondary hydrogenation unit is greater than 2:1 and is less than 100:1.

17. Process according to claim 6, wherein the concentration of water in the liquid reaction composition of the carbonylation reactor is in the range 0.1 to 10 wt %.

18. Process according to claim 6, wherein the concentration of water in the liquid reaction composition of the carbonylation reactor is in the range 1 to 6.5 wt %.

19. Process according to claim 1, wherein the precious metal-based catalyst is a supported catalyst which comprises palladium, rhenium and silver.

20. Process according to claim 9, wherein the secondary hydrogenation unit is operated at a temperature of at least 20° C. lower than the operating temperature of the primary hydrogenation unit.

21. Process according to claim 10, wherein more than 60% and less than 80% of the ethanoic acid introduced into the primary hydrogenation unit is converted into ethanol and ethyl ethanoate per pass.

22. Process according to claim 11, wherein at least 75% of the ethyl ethanoate introduced into the secondary hydrogenation unit is converted into ethanol per pass.

23. Process according to claim 11, wherein at least 90% of the ethyl ethanoate introduced into the secondary hydrogenation unit is converted into ethanol per pass.

24. Process according to claim 11, wherein at least 95% of the ethyl ethanoate introduced into the secondary hydrogenation unit is converted into ethanol per pass.

25. Process according to claim 15, wherein the molar ratio of $H_2$ to ethanoic acid that is introduced into the primary hydrogenation unit is greater than 4:1.

26. Process according to claim 15, wherein the molar ratio of $H_2$ to ethanoic acid that is introduced into the primary hydrogenation unit is greater than 5:1.

27. Process according to claim 15, wherein the molar ratio of $H_2$ to ethanoic acid that is introduced into the primary hydrogenation unit is less than 50:1.

28. Process according to claim 15, wherein the molar ratio of $H_2$ to ethanoic acid that is introduced into the primary hydrogenation unit is less than 15:1.

29. Process according to claim 16, wherein the molar ratio of $H_2$ to [ethyl ethanoate and ethanoic acid] that is introduced into the secondary hydrogenation unit is greater than 4:1.

30. Process according to claim 16, wherein the molar ratio of $H_2$ to [ethyl ethanoate and ethanoic acid] that is introduced into the secondary hydrogenation unit is greater than 5:1.

31. Process according to claim 16, wherein the molar ratio of $H_2$ to [ethyl ethanoate and ethanoic acid] that is less than 50:1.

32. Process according to claim 16, wherein the molar ratio of $H_2$ to [ethyl ethanoate and ethanoic acid] that is introduced into the secondary hydrogenation unit is less than 15:1.

33. Process according to claim 1, wherein the precious metal-based catalyst is a supported catalyst which comprises palladium and rhenium.

34. Process according to claim 1, wherein the precious metal-based catalyst is a supported catalyst which comprises palladium and silver.

* * * * *